United States Patent [19]

Raspanti

[11] Patent Number: 5,338,539
[45] Date of Patent: Aug. 16, 1994

[54] BENZOFURAN DERIVATIVES USEFUL AS SUNSCREENS

[75] Inventor: Giuseppe Raspanti, Bergamo, Italy

[73] Assignee: 3V Inc., Weehawkin, N.J.

[21] Appl. No.: 72,789

[22] Filed: Jun. 7, 1993

[51] Int. Cl.$^5$ .................... A61K 7/42; C07D 405/12; C07D 307/81
[52] U.S. Cl. ........................... 424/59; 424/60; 514/847; 546/196; 549/467
[58] Field of Search .............. 846/196; 549/467; 514/847; 424/59, 60

[56] References Cited

U.S. PATENT DOCUMENTS

| | | | |
|---|---|---|---|
| 4,098,882 | 7/1978 | Lang | 424/59 |
| 4,161,530 | 7/1979 | Koella | 424/274 |
| 5,152,983 | 10/1992 | Nambudiry | 424/60 |

OTHER PUBLICATIONS

Cavier et al "Research on Nitrated Derivatives of Liological; Interest IV" CA 78:381522 (1972).

*Primary Examiner*—Celia Chang
*Attorney, Agent, or Firm*—Griffin, Butler, Whisenhunt & Kurtossy

[57] ABSTRACT

Benzofuran derivatives of formula (I)

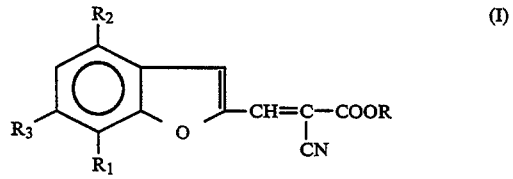

in which R is alkyl, cycloalkyl, aralkyl or a divalent residue which is in its turn linked to a residue which can be obtained from (I) by removing R, highly absorb the sunlight radiations in the UVA region and, in combination with UVB sunscreens, they effectively protect the skin from noxious sunlight radiations.

7 Claims, No Drawings

BENZOFURAN DERIVATIVES USEFUL AS SUNSCREENS

The present invention relates to novel benzofuran derivatives of general formula (I) and the use thereof as sunscreens.

The compounds of the invention have the following formula (I)

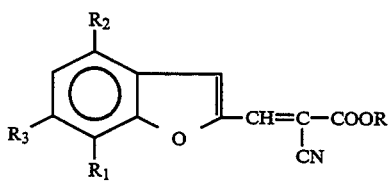
(I)

in which R is $C_1$-$C_{18}$ straight or branched alkyl, $C_5$-$C_{12}$ cycloalkyl, aralkyl, or a group of formula (II), (III) or (IV)

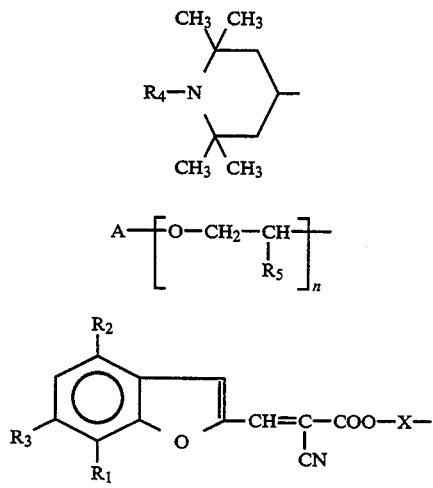

in which
R$_4$ and R$_5$ are hydrogen or methyl;
A is $C_1$-$C_{18}$ straight or branched alkyl, $C_5$-$C_8$ cycloalkyl, optionally substituted aryl, n can be an integer 1 to 10;
X is $C_2$-$C_{18}$ straight or branched alkylene or the divalent residue of formula (V) or (VI)

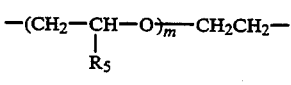

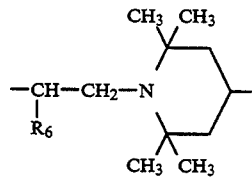

in which
m is an integer 1 to 20 and R$_6$ is hydrogen, methyl or ethyl;
R$_1$ and R$_2$ can be the same or different and are hydrogen or $C_1$-$C_8$ straight or branched alkyl;
R$_3$ is hydrogen or alkoxy.

Ultraviolet radiations of sunlight are known to exert a damaging action on skin tissue. In fact, the prolonged exposure to sunlight is considered to be the main cause in the development of degenerative processes and of some skin tumors.

By using particular compounds, the so-called sunscreens, which are capable of absorbing the UV part of solar radiation, the damaging effect s and the aging of the skin can be prevented or, at least, slowed down.

A number of substances have been studied and tested as protecting agents, and an extensive patent literature exists on this subject, in which compounds belonging to different chemical classes are proposed, which are capable of absorbing in the ultraviolet region, particularly the radiation from 290 to 400 nm.

The radiation from 290 to 320 nm (named UV-B) causes erythema to form, whereas radiation from 320 to 400 nm (named UV-A) is responsible for skin suntan.

Sunscreens adsorbing in the UV-B region are widely used as protecting agent s again st sunburns; whereas the use of sunscreens to shield skin from UV-A radiations was unknown until some time ago, except for some cases of particular therapies.

However, recent researches evidenced that the continued and intensive UV-A radiation can also cause remarkable skin damages and, moreover, it accelerates the aging of the skin.

Only a few of the compounds proposed up to now as sunscreens proved suitable for practical application. Among the se , p-methoxy-cinnamic acid and p-dimethylaminobenzoic acid esters for UVB and; hydroxybenzophenones and dibenzoylmethane derivatives for UVA.

Now it has surprisingly been found that the compounds of formula ( I ) highly absorb sunlight radiations in the UVA region, therefore, in combination with the UVB sunscreens, they can effectively protect the skin from the damaging radiations of sunlight, thus preventing an early aging of the skin.

The compounds of the present invention are prepared according to known methods (Knoevenagel's condensation ) from benzofuran-2-carboxyaldehyde and cyanoacetic acid esters , which are in turn obtained by esterificating cyanoacetic acid or by transesterificating methyl- or ethyl cyanoacetate with the corresponding alcohols.

The compounds of formula (I) in which R is an higher alkyl or a group of formula (II)-(IV) can be conveniently prepared also by transesterificating the compounds of formula ( I ) in which R is methyl or ethyl. The compounds are recovered and, if necessary, purified according to known methods.

D 1087902 , D 2816819 and US 3275520 disclose structurally similar compounds containing the cyanobenzylidene group of the following formula (VII)

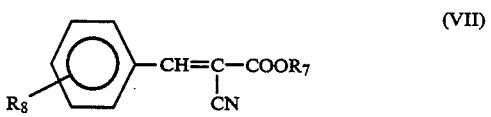
(VII)

in which R$_7$ is alkyl and R$_8$ hydroxy or alkoxy; however, these compounds show a lower absorption in the UVA region than the absorption of the compounds according to the present invention, in which the absorption peaks in the 330-37 0 region are higher than those of 2-hydroxy-4-methoxybenzophenone and also of 4-tert--butyl-4-methoxydibenzoylmethane, which are UVA sun screens used nowadays in the preparation of cosmetic or dermatological formulations.

According to the present invention, the compounds of formula (I) are used preferably in combination with UVB sunscreens for the preparation of cosmetic or dermatological formulations suitable for the protection of the skin exposed to the damaging action of sunlight radiations.

The UVA sun screens of formula (I) can be added, of course also in combination with UVB sunscreens and/or other stabilizers, to the cosmetic formulations, generally in amounts ranging from 0.05 to 15%, preferably from 0.1 to 10% by weight of the cosmetic formulation.

The compounds of formula (I) are added either to protect the formulations themselves, for example to prevent undesired discolorations, or to protect the skin treated with the formulation from the damaging action of sunlight radiations, which cause a premature wrinkled and squamous appearance and sometimes even tumors.

The cosmetic formulations which are added with the light stabilizers according to the present invention, can be of various kinds and they can be used for different purposes. Generally they are in form of ointments, creams, lotions, emulsions and the like.

The following examples illustrate the invention.

EXAMPLE 1

44 g of benzofuran-2-carboxyaldehyde dissolved in 180 ml of toluene are added with 33 q of methylcyanoacetate, 0.8 g of piperidine and 2 g of acetic acid, refluxed and stirred 2 hours, removing the formed water.

The react ion mixture is cooled and the formed precipitate is filtered, washed twice with toluene and dried.

6 g of compound of formula (VIII) with $R = CH_3$ are obtained, in form of a yellow crystalline substance with m.p. 143–145° C. and with E' of 1426 at 359 nm.

Following the procedure de scribed in Example 1, the compounds listed in Table 1 are obtained.

TABLE 1

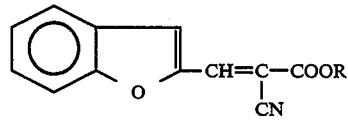
(VIII)

| Example | R | M.p. (°C.) | E' | nm |
|---|---|---|---|---|
| 2 | $C_4H_9-CH(C_2H_5)-CH_2-$ | 50–52° C. | 1100 | 360 |
| 3 | $CH_3-CH(CH_3)-CH_2-$ | 53–55 | 1212 | 360 |
| 4 | $C_2H_5-CH(C_2H_5)-CH_2-$ | 69–71 | 1199 | 360 |
| 5 | (2,2,6,6-tetramethyl-1-methyl-piperidin-4-yl) | 126–128 | 940 | 360 |

EXAMPLE 6

5.2 g of 1,10 decanediol dissolved in 60 ml of xylene are added with 1.45 g of the compound of the Example 1 and 0.1 g of tetrabutyl ortotinate, the mixture is heated slowly to 180° C. distilling xylene at the same time, then stirring is continued for 2 more hours at 180° C. The product is crystallized from a mixture of toluene and octane, to obtain 12 g of compound of formula (IX), with $X=(CH_2)_{10}$, as a whitish substance with m.p. 112–114° C. and with E' of 1229 at 359 nm.

Following the procedure described in Example 6, the compounds listed in Table 2 are prepared.

TABLE 2

(XI) Bis-benzofuran structure: benzofuran-CH=C(CN)-COO-X-OOC-C(CN)=CH-benzofuran

| Example | X | M.p. (°C.) | E' | nm |
|---|---|---|---|---|
| 7 | $-CH_2-C(CH_3)_2-CH_2-$ (with additional $CH_3$) | 162–165 | 1380 | 359 |
| 8 | $CH_2-CH_2-N$(2,2,6,6-tetramethylpiperidin-4-yl) | 241–243 | 1164 | 361 |
| 9 | $-(CH_2-CH_2-O)_2-CH_2-CH_2-$ | 143–145 | 1293 | 360 |

EXAMPLE 10

Preparation of a sun cream

A mixture consisting of 10 g of cyclodimeticone/dimeticone copolymer (Dow Corning Q 2-3223), 10 g of cyclometicone (Dow Corning 344), 0.5 g of polysorbate 20 (Tween 20) and 2 g of the compound of Example 9 is prepared.

This mixture is added to a previously prepared solution of 0.2 g of 1,1'-methylene-bis-3-(3'-hydroxymethyl- 2,4-dioxy-imidazolidinyl)urea, 0.05 g of methyl paraben and 77.25 g of water.

I claim:

1. A compound of formula (I)

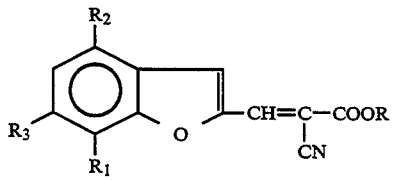
(I)

in which R is $C_1$-$C_{18}$ straight or branched alkyl, $C_5$-$C_{12}$ cycloalkyl, or a group of formula (II), (III) or (IV)

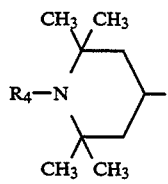
II

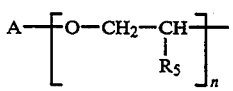
III

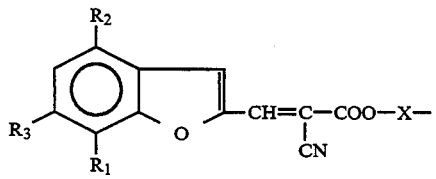
IV in which $R_4$ and $R_5$ are hydrogen or methyl;

A is $C_1$-$C_{18}$ straight or branched alkyl, $C_5$-$C_8$ cycloalkyl, n can be an integer 1 to 10;

X is $C_2$-$C_{18}$ straight or branched alkylene or the divalent residue of formula (V) or (VI)

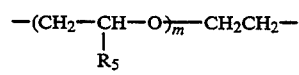
V

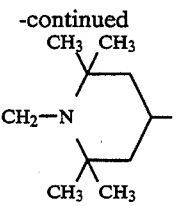
VI in which m is an integer 1 to 20 and $R_6$ is hydrogen, methyl or ethyl;

$R_1$ and $R_2$ can be the same or different and are hydrogen or $C_1$-$C_8$ straight or branched alkyl;

$R_3$ is hydrogen or lower alkoxy.

2. The compounds of claim 1 where $R_1$, $R_2$ and $R_3$ are hydrogen and R is selected from the group consisting of $C_4H_9$—CH($C_2H_5$)—$CH_2$—, $CH_3$—CH($CH_3$)—$CH_2$—, $C_2H_5$—CH($C_2H_5$)—$CH_2$—, and

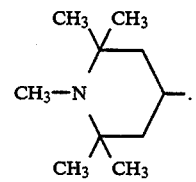

3. The compounds of claim 1 wherein $R_1$, $R_2$ and $R_3$ are hydrogen, R is formula (IV) and X is selected from the group

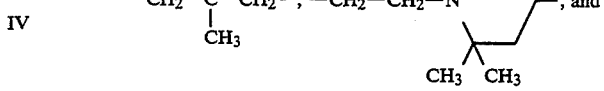, and

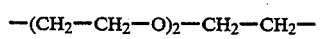

4. Cosmetic or dermatological compositions containing a cosmetic or dermatological carrier and from about 0.05 to about 15% by weight of at least one of the compounds according to claim 1.

5. Cosmetic or dermatological compositions containing a cosmetic or dermatological carrier and from about 0.1 to about 10% by weight of at least one of the compounds according to claim 1.

6. A method for the protection of skin from ultraviolet radiations of sunlight, comprising applying to the skin an ultraviolet radiation absorbing effective amount of a cosmetic or dermatological composition having from about 0.05 to about 15% by weight of at least one of the compounds according to claim 1.

7. The method of claim 6 wherein the composition is a dermatological composition.

* * * * *